(12) United States Patent
Johnson et al.

(10) Patent No.: US 9,839,749 B2
(45) Date of Patent: Dec. 12, 2017

(54) INTRAOCULAR PRESSURE SENSING SYSTEMS, DEVICES, AND METHODS

(71) Applicant: Novartis AG, Basel (CH)

(72) Inventors: Andrew David Johnson, Laguna Niguel, CA (US); Pooria Sharif Kashani, Irvine, CA (US)

(73) Assignee: Novartis AG (CH)

( * ) Notice: Subject to any disclaimer, the term of this patent is extended or adjusted under 35 U.S.C. 154(b) by 0 days.

(21) Appl. No.: 15/139,799

(22) Filed: Apr. 27, 2016

(65) Prior Publication Data

US 2017/0312431 A1    Nov. 2, 2017

(51) Int. Cl.
| | |
|---|---|
| *A61B 1/06* | (2006.01) |
| *A61M 5/172* | (2006.01) |
| *A61F 9/007* | (2006.01) |
| *A61B 1/07* | (2006.01) |
| *A61M 3/02* | (2006.01) |
| *A61M 1/00* | (2006.01) |
| *A61B 3/16* | (2006.01) |

(52) U.S. Cl.
CPC ............ *A61M 5/1723* (2013.01); *A61B 1/07* (2013.01); *A61B 3/16* (2013.01); *A61F 9/007* (2013.01); *A61F 9/00736* (2013.01); *A61M 1/0031* (2013.01); *A61M 3/0279* (2013.01); *A61M 2205/3344* (2013.01)

(58) Field of Classification Search
CPC ............ A61M 5/1723; A61M 1/0031; A61M 3/0279; A61M 2205/3344; A61B 1/07; A61B 3/16; A61F 9/007; A61F 9/00736

USPC ................ 600/249, 398, 488, 561
See application file for complete search history.

(56) References Cited

U.S. PATENT DOCUMENTS

| | | | | |
|---|---|---|---|---|
| 4,548,205 A | * | 10/1985 | Armeniades | A61B 3/16 600/488 |
| 4,841,984 A | * | 6/1989 | Armeniades | A61B 3/16 600/561 |
| 5,830,176 A | * | 11/1998 | Mackool | A61F 9/00745 604/22 |
| 2004/0254438 A1 | * | 12/2004 | Chuck | A61B 3/16 600/398 |
| 2009/0146583 A1 | * | 6/2009 | Bhadri | A61B 3/0008 315/294 |
| 2011/0160561 A1 | | 6/2011 | Hastings et al. | |
| 2012/0253165 A1 | | 10/2012 | Yen et al. | |
| 2015/0148836 A1 | | 5/2015 | Heeren | |

FOREIGN PATENT DOCUMENTS

EP    0180317 A1    5/1986

* cited by examiner

*Primary Examiner* — Pedro Philogene
*Assistant Examiner* — David C Comstock
(74) *Attorney, Agent, or Firm* — Kenneth D. Bassinger (57) ABSTRACT

An ophthalmic surgical system enabling pressure measurements proximal to the eye may include an illumination probe having a probe tip configured for insertion through an incision in an eye of a patient. The probe tip may include a distal end of an optical fiber, wherein the distal end of the optical fiber includes a first reflective surface and a second reflective surface. The first and second reflective surfaces being separated by a cavity, wherein the second reflective surface is provided by a partially transparent wall forming an exterior surface of the distal end of the optical fiber.

12 Claims, 11 Drawing Sheets

Fig. 9 ured as being representative of the pressure at a distal
INTRAOCULAR PRESSURE SENSING SYSTEMS, DEVICES, AND METHODS

TECHNICAL FIELD

The present disclosure is directed to systems, devices, and methods for determining the pressure in a cavity during minimally invasive surgery. In particular, the present disclosure is directed to systems, devices, and methods for measuring a patient's intraocular pressure (IOP).

BACKGROUND

During typical vitreoretinal surgical procedures a portion of the vitreous within the vitreous chamber is removed to allow access to the retina or other parts of the eye. Removal of the vitreous is accompanied by an infusion of fluid to maintain the shape of the eye and to maintain an appropriate intraocular pressure level within the eye. The intraocular pressure (IOP) of the eye is calculated based on both the atmospheric pressure and the estimate of pressure within the eye.

In some current approaches, the estimate of IOP is derived based on measurements from a pressure sensor located on a surgical console that is a distance from the eye. For example, the pressure at a proximal end of an infusion line may be measured as being representative of the pressure at a distal end of the infusion line. Factors such as a flow resistance and time delays introduce error into such measurements.

The potential for delays and inaccuracies resulting from measuring pressure at locations apart from the eye renders some approaches unsatisfactory. Therefore, a need exists for improved systems, devices, and methods for measuring intraocular pressure during ophthalmic surgery.

SUMMARY

The present disclosure is directed to systems, devices, and methods of monitoring a pressure within an eye during a medical procedure.

Exemplary medical systems and devices are provided herein. An exemplary ophthalmic surgical system enabling pressure measurement proximal to the eye may include an illumination probe having a probe tip configured for insertion through an incision in an eye of a patient. The probe tip may include a distal end of an optical fiber, wherein the distal end of the optical fiber includes a first reflective surface and a second reflective surface. The first and second reflective surfaces being separated by a cavity, wherein the second reflective surface is provided by a partially transparent wall forming an exterior surface of the distal end of the optical fiber.

An exemplary ophthalmic device for performing operations within an eye of a patient may include an infusion cannula support structure having a proximal end configure to couple to flexible tubing and an elongate tubular member extending from a distal end of the infusion cannula support structure. The elongate tubular member may have a central lumen extending therethrough. The ophthalmic device may further include a pressure sensor disposed proximate to the elongate tubular member such that when a distal end of the elongate tubular member is positioned within the eye the pressure sensor is also positioned within the eye.

An exemplary infusion line for providing fluid to an ophthalmic surgical site may include an infusion cannula support structure and a rigid elongate tubular member extending distally from the infusion cannula support structure. The elongate tubular member may be sized for insertion through an incision in an eye of a patient. The infusion line may also include flexible tubing that extends from the infusion cannula support structure to a proximal connector and a pressure sensor disposed between the elongate tubular member and the proximal connector.

An exemplary infusion valve for liquid/gas exchange during an ophthalmic surgery is provided and may include a valve body and a valve mechanism disposed within the valve body, wherein the valve mechanism is configured to facilitate transitions between gas infusion and liquid infusion. The infusion valve may further include a first inlet connector coupled to a gas source, a second inlet connector coupled to a liquid source, an outlet connector for connection to an infusion line, and a pressure sensor affixed to the valve body.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the accompanying drawings and the following detailed description.

BRIEF DESCRIPTION OF THE DRAWINGS

The accompanying drawings illustrate implementations of the instruments, systems, and methods disclosed herein and together with the description, serve to explain the principles of the present disclosure.

DETAILED DESCRIPTION

Reference is now made in detail to the exemplary embodiments of the invention, examples of which are illustrated in the accompanying drawings. Wherever possible, the same reference numbers are used throughout the drawings to refer to the same or like parts.

The present disclosure is directed to systems, devices, and methods for measuring pressure within the eye of a patient. Pressure may be measured during an ophthalmic procedure and may be used by an ophthalmic surgical system in the control of various subsystems of the ophthalmic surgical system. For example, when a measured pressure within the eye exceeds a threshold value, an exemplary ophthalmic surgical system may control a fluidics subsystem to decrease the flow of fluid into the eye. Conventional approaches may attempt to measure a proxy value of the pressure in the eye by measuring pressure at a proximal end of an infusion line located a distance from the eye.

Systems, devices, and methods provided herein facilitate the collection of more accurate pressure measurement by measuring the pressure directly in the eye or along the infusion line, closer to the eye than conventional systems. The systems and devices may include different types of pressure sensors. For example, some implementations may include optical fiber based pressure sensors while others may include various microelectromechanical-systems-based (MEMS-based) pressure sensors. Including the pressure sensor within the eye or within several inches of the eye may provide more accurate pressure measurements which may be used to determine a patient's intraocular pressure (IOP). The surgical system may include a control unit or other controller to convert the measured pressure to IOP in order to provide an accurate indication of the state of the eye at a particular time. Converting the measured pressure to IOP may include detecting the atmospheric pressure and calculating the IOP based on both the atmospheric pressure and the measured pressure since IOP is a function of both atmospheric and eye pressure.

Many surgeries are performed while maintaining the eye at a desired elevated IOP in order to reduce any chance of collapse. To provide this desired IOP, fluid may be provided into the eye via an infusion line at an appropriate rate. The measured pressure may be used by the ophthalmic surgical system to automatically make adjustments to infusion rates or to drainage rates from the eye. Responding promptly to changes in the measured pressure may prevent unwanted deviations from the desired IOP.

Figure 1:
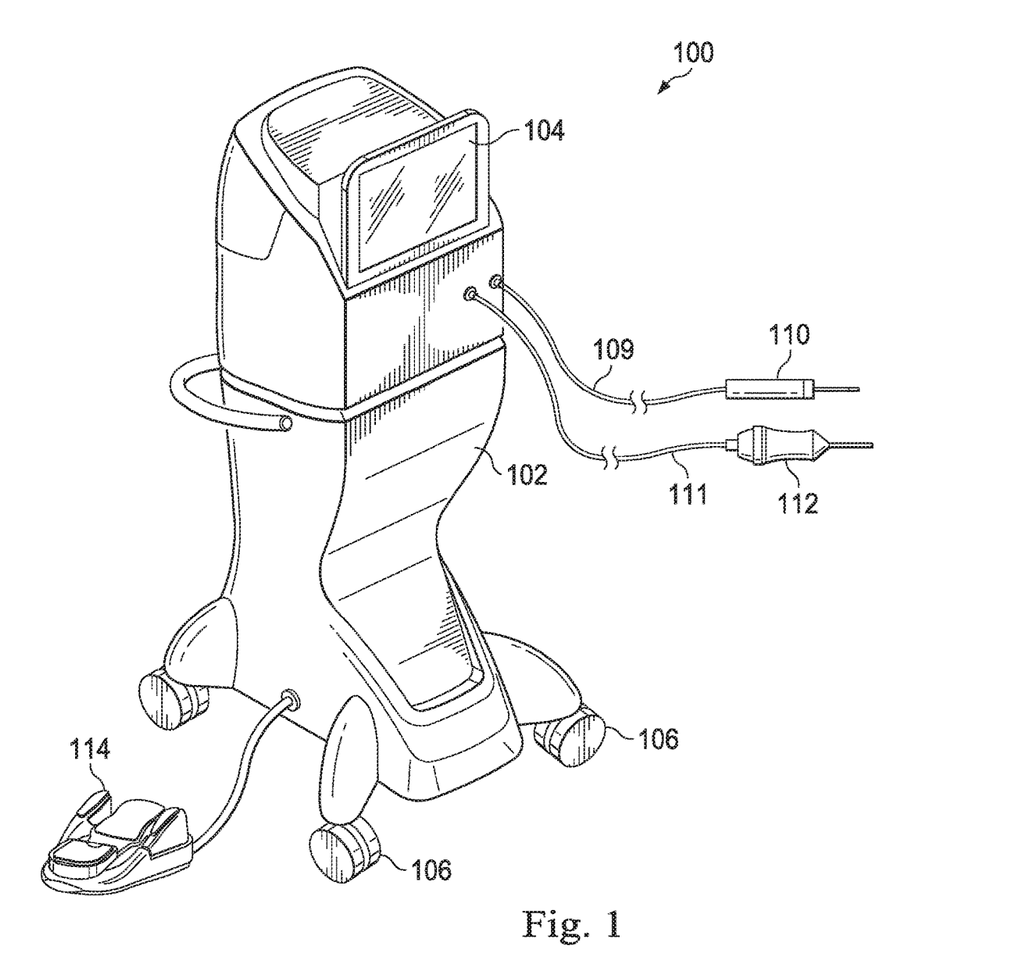
FIG. 1 illustrates a perspective view of a surgical system.

FIG. 1 illustrates an exemplary implementation of an ophthalmic surgical system, generally designated as surgical system 100. While the present disclosure applies to many different types of surgical systems other than the ophthalmic surgical system 100, the surgical system 100 is described herein to provide appropriate context for the instruments, systems, and methods described herein. As illustrated, the surgical system 100 includes a base housing or console 102 and an associated display screen 104 that may be used to show data relating to system operation and performance during an ophthalmic surgical procedure. The console 102 typically contains several subsystems that cooperate to enable a surgeon or other user to perform a variety of surgical procedures, such as ophthalmic surgical procedures. Exemplary subsystems are described below in greater detail in connection with FIG. 2.

The surgical system 100 is illustrated as including multiple surgical instruments or devices. These devices may be coupled to the console 102 by conduits and may form part of the surgical system 100. The devices 110 and 112 represents any number of medical and/or surgical instruments or devices, including, for example, a vitrectomy probe, an illumination probe, an aspiration probe, an irrigation/infusion probe, a drainage cannula, a phacoemulsification probe, a diathermy probe, or other types of medical instruments. As illustrated in FIG. 1, the device 110 may be an infusion cannula and the device 112 may be an illumination probe. Accordingly, the device 110 may be referred to herein as infusion device and the device 112 may be referred to as an illumination probe or as an illumination device. Implementations of the devices 110 and 112 may include one or more hand pieces, such that either or both of the devices 110 and 112 are configured to be held comfortably in a user's hand for manipulation thereby. In other implementations, either or both of the devices 110 and 112 may be configured to be secured proximate the eye of a patient so that the surgeons other hands are free to utilize other instruments and devices and performing a procedure.

The devices 110 and 112 may be coupled to one or more subsystems included in the console 102. For example, the infusion device 110 may be coupled to a fluidics subsystem 120 (see FIG. 2) that facilitates control of a pump and/or a vacuum for use in the providing one or more fluids such as a gas (e.g., air or another suitable gas) or a liquid, such as a balanced salt solution, into the eye of the patient. The illumination device 112 may be coupled to an instrument subsystem 130 (see FIG. 2) that may include a light source and or other optical components. In some embodiments, an instrument subsystem 130 (see FIG. 2) may also provide power to the illumination device 112 and control operation of the illumination device 112.

The surgical system 100 further includes conduits that supply the devices 110 and 112. A conduit 109 couples the infusion device 110 to the console 102, while a conduit 111 couples the illumination device 112 to the console 102. The conduits 109 and 111 may include cables, tubes, wires, fibers, or conductors, among other carriers, to provide for the operation of the devices 110 and 112. Some implementations of the surgical system 100 may further include a foot pedal 114 which can be manipulated by a user to control various aspects of the surgical system 100, including operational parameters, such as flow rates, speeds, irrigation or aspiration, light intensity, and/or other parameters of the devices 110 and 112.

The devices 110 and 112 may be used in any of a variety of ophthalmic procedures, such as an anterior segment procedure, a posterior segment procedure, a vitreoretinal procedure, a vitrectomy procedure, a cataract procedure, and/or other procedures. Surgical procedures other than these ophthalmic procedures may be performed by the surgical system 100 and the device 110 and/or the device 112.

Figure 2:
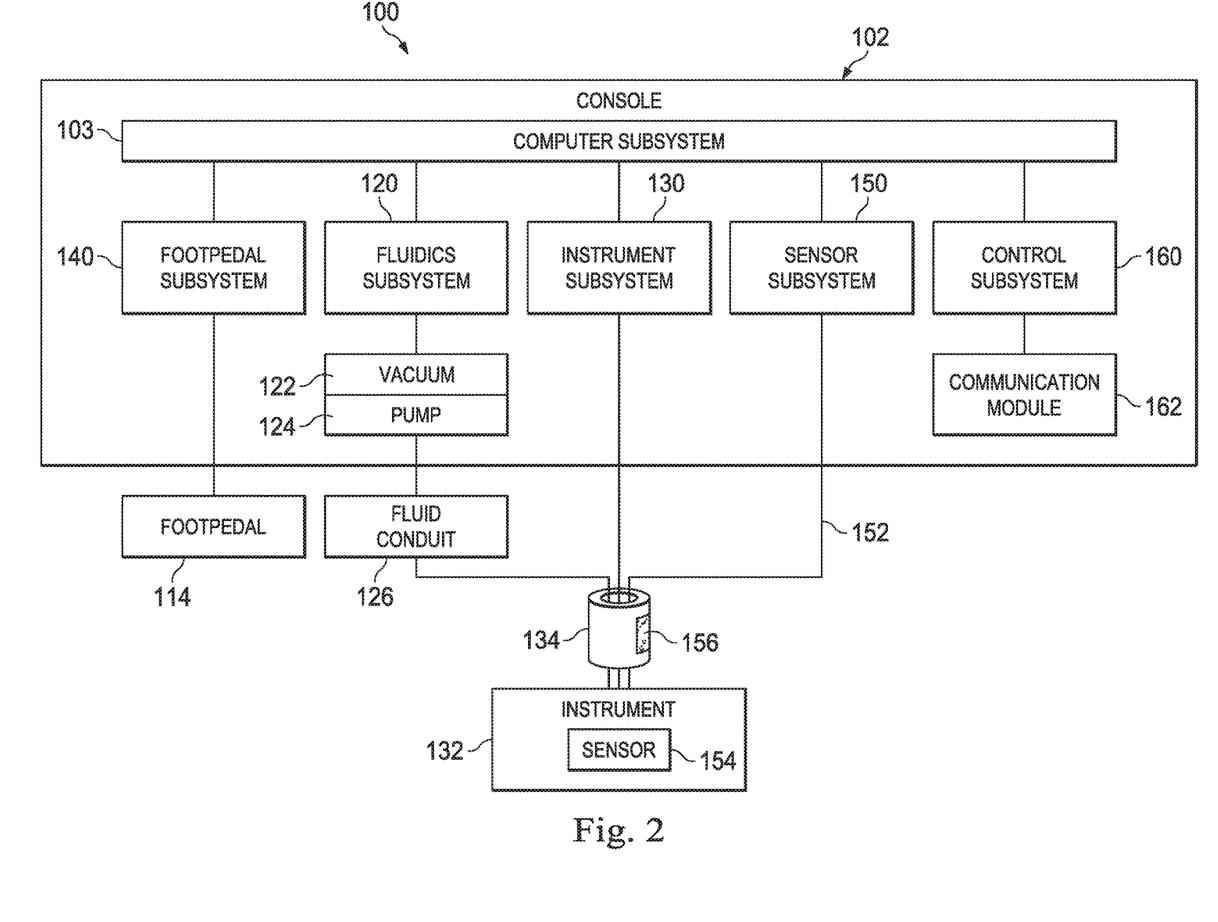
FIG. 2 is an illustration of a block diagram of the surgical system of FIG. 1.

FIG. 2 is a block diagram according to an exemplary implementation of the surgical system 100. The surgical system 100 may include the console 102 and several subsystems contained therein. In this example, the console 102 includes a computer subsystem 103 configured to communicate with the display screen 104 (FIG. 1) and with a number of subsystems that are used together to perform ophthalmic surgical procedures, such as vitreoretinal surgical procedures, for example. The computer subsystem 103 may include one or more processing devices, such as a central processing unit, microcontroller, or central processor, and a data storage system. The data storage system may include one or more types of memory, such as RAM, ROM, flash memory, a disk-based hard drive, and/or a solid-state hard drive. The processing devices and data storage system may communicate over a bus, which may also permit communication with and between one or more of the subsystems of the surgical system 100.

Some examples of subsystems in the implementation shown in FIG. 2 may include a fluidics subsystem 120, an instrument subsystem 130, and a foot pedal subsystem 140 including, for example, the foot pedal 114. The fluidics subsystem 120 may provide an aspiration pressure source, including a vacuum 122 and/or a pump 124. The pump 124 may be coupled to a gas source and or a liquid source and may be configured to pump the gas or liquid through a fluid conduit 126 to the eye of a patient. The fluid conduit 126 or a portion thereof may extend between the console 102 and an exemplary instrument 132 through the conduit 134 (FIG. 1). The exemplary instrument 132 may represent either or both of the devices 110 and 112 of FIG. 1. Additionally, the conduit 134 may represent either or both of the conduits 109 and 111 of FIG. 1. The surgical system 100 may further include a control subsystem 160 that is coupled to a communication module 162. The control subsystem 160 and the communication module 162 may facilitate control of the device 110 and/or the subsystems and other features illustrated in FIG. 2, such as control of the vacuum 122 and the pump 124 of the fluidics subsystem 120.

As illustrated in FIG. 2, the surgical system 100 may further include a sensor subsystem 150 that is configured to receive signals from sensors and interpret those signals. As illustrated, the sensor subsystem 150 includes a communication channel 152 to facilitate communication with a sensor 154 and/or a sensor 156. The sensor 154 may be disposed on or within the exemplary instrument 132. The sensor 156 may be disposed on or in a wall of the conduit 134. The communication channel 152 may be a wire or collection of wires, in some implementations. In other implementations, the communication channel 152 may be a wireless communication channel such as a Wi-Fi, Bluetooth®, or other communication channel. Either or both of the sensors 154 and 156 may be a pressure sensor. Suitable pressure sensors include optical fiber pressure sensors and/or MEMS pressure sensors, which may have a diaphragm or cantilever structure formed by MEMS fabrication techniques. Other types of pressure sensors are also suitable.

Figure 3:
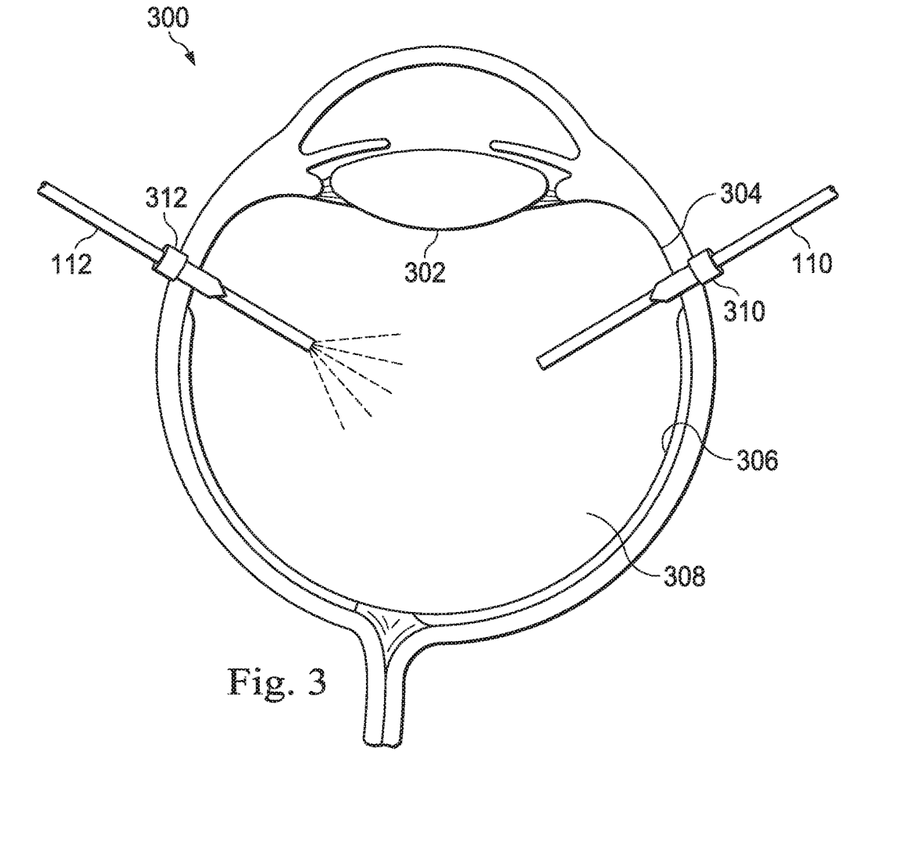
FIG. 3 is an illustration of surgical devices in situ in an eye.

FIG. 3 shows distal portions of the devices 110 and 112 as inserted into an eye 300 during the performance of a surgical procedure. The eye 300 includes several components including the lens 302, the sclera 304, and the retina 306. The posterior segment of the eye is filled with vitreous humor 308, which may be partially removed during the procedure. As illustrated in FIG. 3, the device 110 is an infusion cannula and the device 112 is an illumination probe. Both of the devices 110 and 112 include an elongate tubular member which may be less than a millimeter in diameter and sized for insertion through the entry cannulas 310 and 312, which can be placed into an opening made in the sclera 304 to provide access to the posterior chamber of the eye 300. For example, the devices 110 and 112 may include elongate tubular members that have an outer diameter less than 0.6 mm, with an inner diameter that is less than about 0.3 mm. The elongate tubular member may be a 25 gauge needle or a higher gauge needle. The illumination device 112 may provide light into the posterior chamber of the eye 300 to enable a surgeon to view material within the posterior chamber such as the vitreous humor and or the retina 306. The device 110 may provide fluid, such as a salt solution into the eye to ensure the eye 300 retains and shape during a procedure. Implementations of the devices 110 and 112 may each or both include a pressure sensing system to provide measurements of the pressure within the posterior chamber of the eye 300.

Figure 4A:
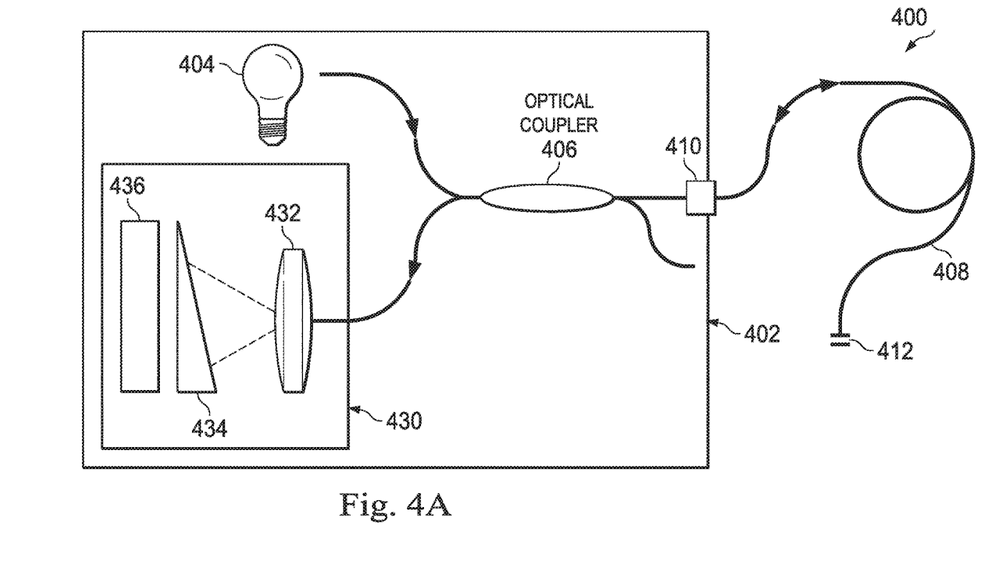
FIG. 4A is an illustration of an optical fiber pressure sensing system.

FIG. 4A is an illustration of an optical fiber pressure sensing system 400 that may be included in the exemplary surgical system of FIG. 1. The pressure sensing system 400 includes a signal conditioner 402 which may be disposed within the housing of the console 102 (FIG. 1). The signal conditioner 402 may be an embodiment of the sensor subsystem 150 (FIG. 2). The signal conditioner 402 may include a light source 404. In some instances, the light source 404 may include a halogen tungsten lamp, a high pressure arc lamp (e.g., using metal-halides or xenon), a light emitting diode (LED), a laser, or other light source. Light generated by the light source 404 may be transmitted into a two-by-two optical coupler 406 via an optical fiber or another optical channel extending therebetween. In some implementations, the light may pass through one or more optical elements, such as, for example, one or more lenses, mirrors, and/or attenuators, before or after entering optical coupler 406. The optical coupler 406 may be coupled to an optical fiber 408 by an optical connector 410. The optical connector 410 may be secured to a wall of the signal conditioner 402 and may facilitate connection with the optical fiber 408.

Figure 4B:
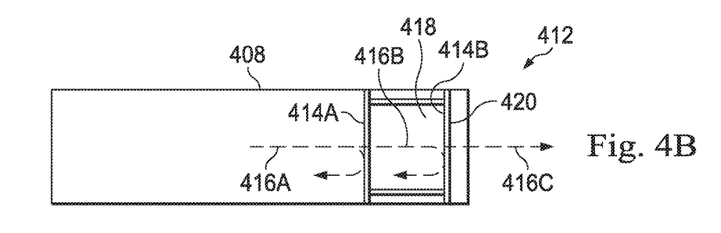
FIG. 4B illustrates a distal end of a pressure sensing optical fiber.

The optical fiber 408 may include an optical fiber pressure sensor 412 at a distal tip thereof. The optical fiber 408 and the optical fiber pressure sensor 412 may range in diameter from about 0.05 mm to about 0.250 mm. Other dimensions are also contemplated. In some implementations, the optical fiber pressure sensor 412 may be a Fabry-Perot type pressure sensor. As shown in FIG. 4B, the optical fiber 408 includes at least two reflective surfaces at the distal end thereof. The reflective surfaces are referred to collectively as reflective surfaces 414. The first reflective surface 414A may cause a first reflection 416A to be directed back toward the optical coupler 406, while transmitting a portion of the incident light. Located distally from the first reflective surface 414A is a cavity 418. The cavity 418 may a Fabry-Perot cavity and may be filled with air or another gas or may be a vacuum sealed chamber. The second reflective surface 414B defines a distal side of the cavity 418 and causes a second reflection 416B to be directed back toward the optical coupler 406, like the first reflection 416A. The second reflective surface 414B is provided by a wall 420 which is partially transparent. Although a portion of light incident upon the second reflective surface 414B is directed back toward the optical coupler 406, another portion of the light incident upon the second reflective surface 414B is transmitted through the wall 420 and into the posterior chamber of the eye 300 (FIG. 3). This transmitted light 416C may permit a surgeon to visualize features within the posterior chamber of the eye 300.

In this example, the first and second reflections 416 travel back along the optical fiber 408 toward the optical coupler 406. The optical coupler 406 directs the backward traveling light to the signal capture device 430. The signal capture device 430 includes optical components 432, which may include lenses, mirrors, and/or filters. The signal capture device 430 may further include an optical wedge 434 and an image capture device 436. The optical wedge 434 may be an optical flat or multiple optical flats that are formed with a slight angle. The image capture device 436 may be a charge-coupled device (CCD), a complementary metal-oxide semiconductor (CMOS) based image sensor, or another comparable type of image capture device.

In this example, the image capture device 436 captures interference signals produced by an interference or phase difference between the first reflection 416A and the second reflection 416B. The interference signal is processed by an image processor or a central processing unit of the computer subsystem 103 or by a suitable processor contained as a component within the sensing system 400. As the distance between the first reflective surface 414A and the second reflective surface 414B changes, the interference signal changes. The distance between the reflective surfaces 414 may change according to the pressure present within the eye 300 of FIG. 3. For example, as a pressure within the eye 300 increases the wall 420 may flex, such that the size of the cavity 418 (and the distance between the reflective surfaces 414) decreases. Through a calibration process, the interference signal can be interpreted by the computer subsystem 103 or by the sensor subsystem 150 of the surgical system 100 (FIGS. 1 and 2) as indicative of a particular measured pressure level.

The pressure sensing system 400, with the optical fiber pressure sensor 412 may be implemented as an illumination probe, such as the device 112 of FIG. 1 and as shown in FIG. 3. The illumination probe may facilitate the placement and positioning of the distal end of the optical fiber pressure sensor 412 within the body cavity of a patient, such as the eye 300. Some implementations of exemplary illumination probes may include an optical fiber pressure sensor and an additional optical fiber to provide illumination. In other disclosed implementations, the optical fiber pressure sensor 412 may be incorporated into devices other than illumination probes. Some implementations of the pressure sensing system 400 may be included alongside a conventional illumination fiber in a pressure sensing implementation of the illumination device 112. Such an implementation may include a first optical fiber that is configured as a pressure sensing optical fiber and may further include a second optical fiber that is configured to provide illumination within a chamber. Both of the fibers may extend through and be deployable from an outer elongate tubular member having a central lumen or having multiple lumens. The two optical fibers may be coupled together to be deployed together from an elongate tubular member. Such an implementation may be similar, in some respects, to the exemplary infusion device 500 of FIG. 5A.

Figure 5A:
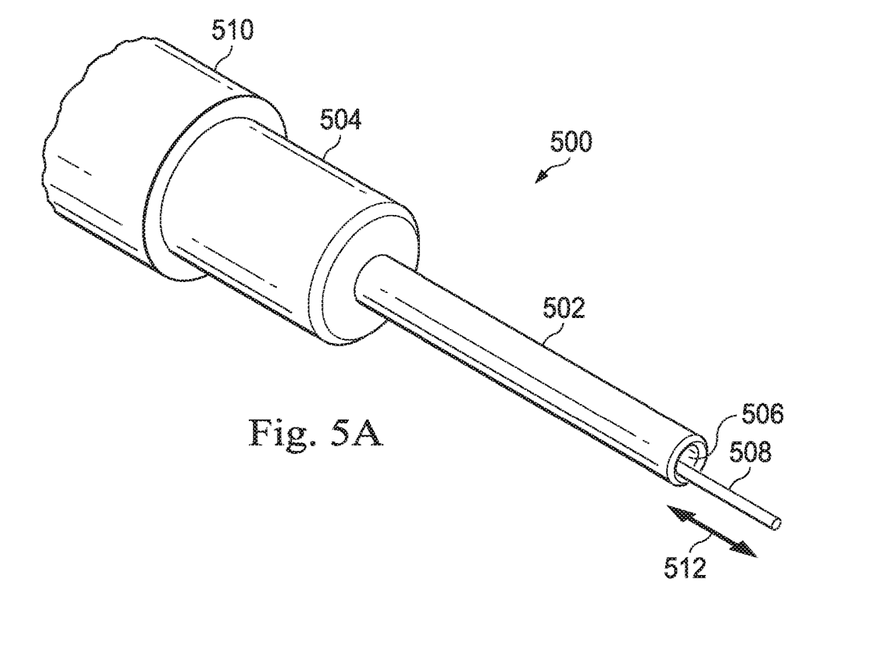
FIG. 5A illustrates the pressure sensing optic fiber of FIG. 4B as deployed in an infusion device.

FIG. 5A illustrates the exemplary optical fiber pressure sensor 412 of FIG. 4B as deployed in an exemplary infusion device 500. The infusion device 500 may be similar to the device 110 described above in connection with FIGS. 1 and 3. The infusion device 500 may include an elongate tubular member 502 that extends distally from an infusion cannula support structure 504. Both the elongate tubular member 502 and the support structure 504 may be formed from a rigid material, such as stainless steel or a rigid polymeric material. The elongate tubular member 502 includes a lumen 506 through which an optical fiber pressure sensor 508 may be introduced into the anterior chamber of the eye 300. The optical fiber pressure sensor 508 may be a Fabry-Perot type pressure sensor like the pressure sensor 412 of FIGS. 4A and 4B. While some implementations may include a wall 420 (FIG. 4B) that is partially transparent to provide illumination into the eye 300, other implementations may include a wall 420 that is opaque or a second reflective surface 414B on the wall 420 that does not permit any light to pass through. The support structure 504 may couple to a flexible tubing 510 that may extend between the support structure 504 and the console 102 (of FIG. 1.) Accordingly, the flexible tubing 510 may be the conduit 109 shown in FIG. 1.

The support structure 504 may include a member that is insertable into a lumen of the flexible tubing 510 and/or, the support structure 504 may be affixed to the flexible tubing 510 by an adhesive. As illustrated by the arrow 512, the optical fiber pressure sensor 508 may be extended from the lumen 506 such that a distal end of the optical fiber pressure sensor 508 extends beyond the distal end of the elongate tubular member 502. Similarly, the optical fiber pressure sensor 508 may be retracted into the lumen 506 such that the distal end of the pressure sensor 508 does not extend beyond the elongate tubular member 502.

For example, when the elongate tubular member 502 is extended through an entry cannula, like the entry cannula 310 of FIG. 3, the distal tip of the optical fiber pressure sensor 508 may be positioned within the lumen 506 to prevent damage to the pressure sensor 508 during insertion. Thereafter, the surgeon or another operator may cause the pressure sensor 508 to protrude from the lumen 506. Measurement accuracy may be increased by deploying the pressure sensor 508 outside the lumen 506.

Figure 5B:
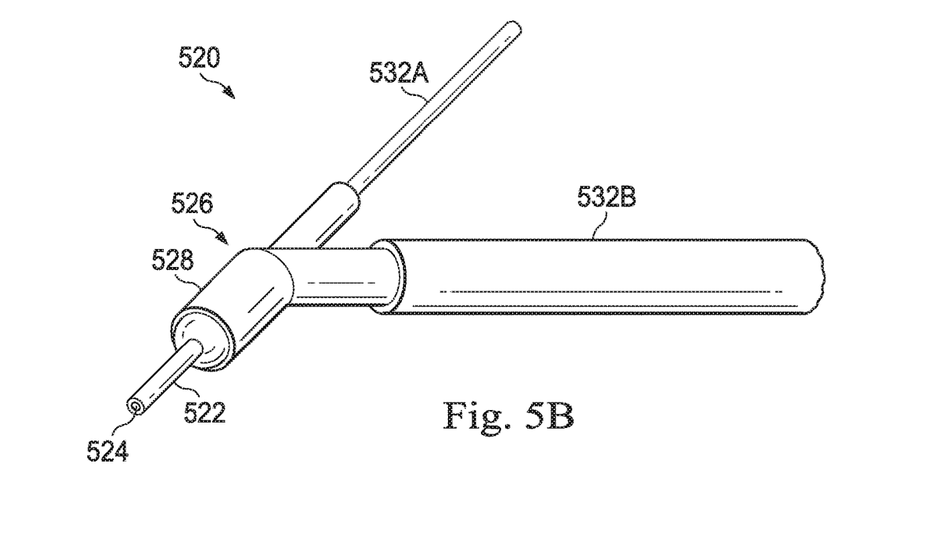
FIGS. 5B, 5C, and 5D illustrate implementations of infusion devices including the pressure sensing optical fiber of FIG. 4B.
Figure 5C:
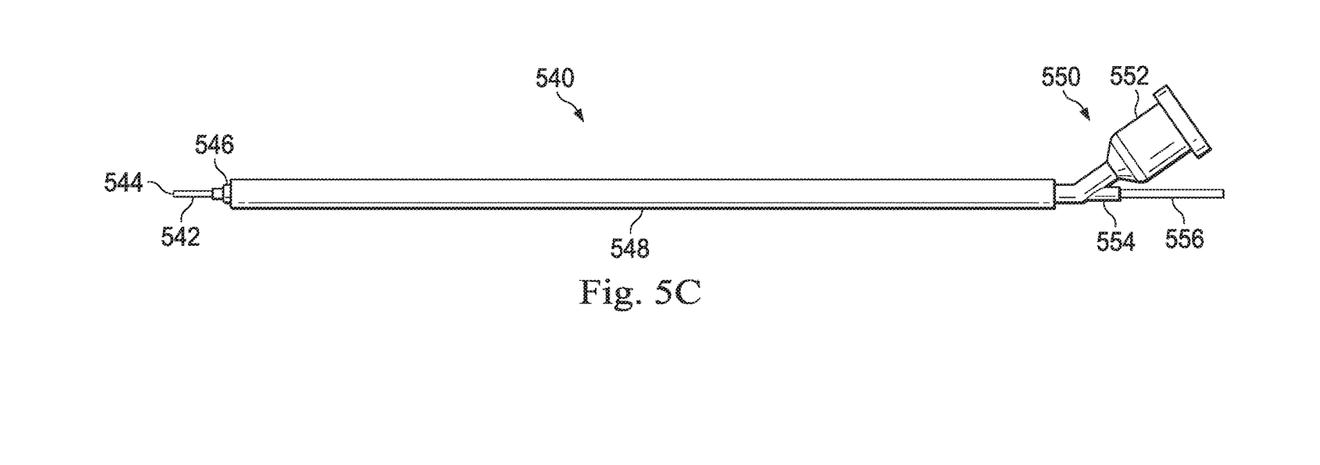
Figure 5D:
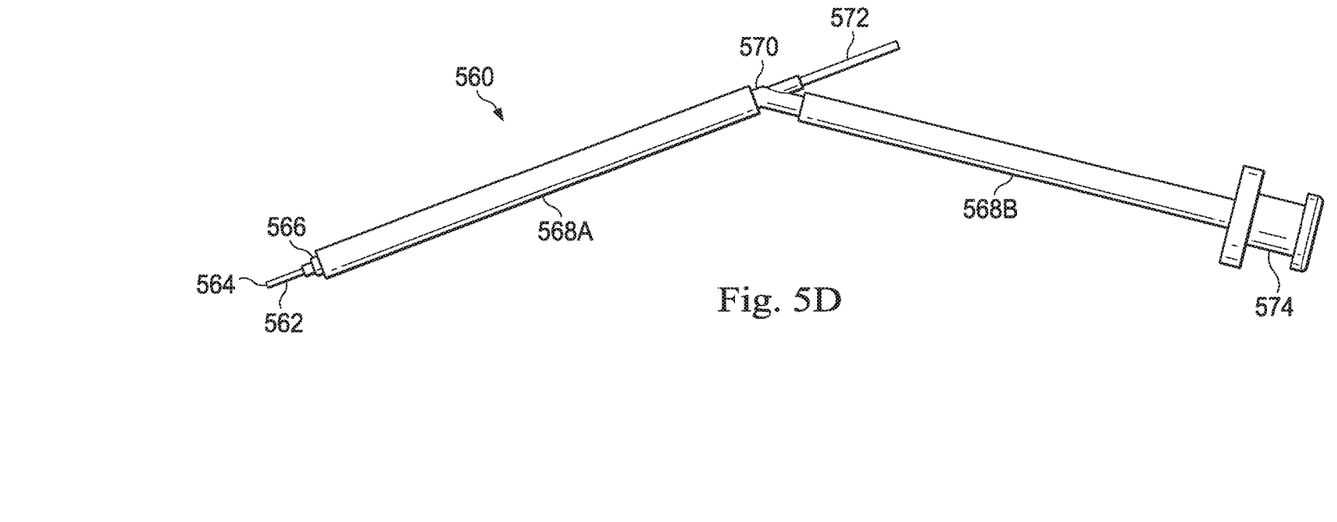

FIGS. 5B, 5C, and 5D illustrate exemplary implementations of infusion devices including the exemplary optical fiber pressure sensor 412 of FIG. 4B. The infusion device 520 includes an elongate tubular member 522 having a lumen 524 therein. The lumen 524 may permit fluids such as gases or liquids to be introduced into the eye 300. Additionally, an optical pressure sensor may be disposed within the lumen 524 or may be passed through the lumen 524 into the anterior chamber of the eye 300. The device 520 includes a compression fitting structure 526 that receives a portion of a support structure 528. The support structure may be formed integrally with the elongate tubular member 522. The compression fitting structure 526 may have multiple lumens, including a lumen sized and configured to receive the support structure 528. The multiple lumens also permit connection to an optical fiber tubing 532A and to a flexible tubing 532B. Each of the tubings 532A and 532B couples to a proximal lumen of the compression fitting structure 526. These proximal lumens joined together within the compression fitting structure 526 to form a single distal lumen. The support structure 528 may be insertable or otherwise coupleable into a single distal lumen of the compression fitting structure 526. The pressure sensor may be insertable through the optical fiber tubing 532A, through the compression fitting structure 526 and thereby into the lumen 524 of the elongate tubular member 522. The compression fitting structure 526 may sealingly couple to the optical fiber tubing 532A, the flexible tubing 532B, and the support structure 528, such that leakage at the compression fitting structure 526 may be prevented. Flexible tubing 532B may permit the introduction or aspiration of fluid and/or gas to or from the eye 300

FIG. 5C depicts an infusion device 540 that may be similar in many respects to the devices 500 and 520 of FIGS. 5A and 5B, respectively. The infusion device 540 includes an elongate tubular member 542 having a lumen 544 extending therethrough. The elongate tubular member 542 extends distally from the support structure 546. The support structure 546 is coupled to flexible tubing 548. In some implementations, the flexible tubing 548 may be press fit onto the support structure 546. Alternatively or additionally, the flexible tubing 548 may be affixed to the support structure 546 by an adhesive at the distal end of the flexible tubing 548. The proximal end of the flexible tubing 548 may be coupled to a compression fitting structure 550. The compression fitting structure 550 facilitates the coupling of multiple components to permit an optical fiber pressure sensor to pass through a lumen of the flexible tubing 548 while also permitting fluids to pass through the lumen of the flexible tubing 548. The compression fitting structure includes a connector 552, which may be a luer-type connector, and a connector 554. The connector 552 may be coupled to a fluid source or to another tubing or conduit that connects to a fluid source. The connector 554 may receive an optical fiber tubing 556 through which the optical fiber pressure sensor may be passed. In some implementations, the optical fiber pressure sensor 412 of FIGS. 4A and 4B may be passed through the optical fiber tubing 556, through the connector 554 of the compression fitting structure 550, through the lumen of the flexible tubing 548, and through the lumen 544 of the elongate tubular member 542, in order to be introduced into the eye 300.

Referring now to FIG. 5D, shown therein is another implementation of an infusion device according to aspects of the present disclosure. The infusion device 560 may include an elongate tubular member 562 having a lumen 564 extending therein. The elongate tubular member 562 may be coupled to a support structure 566. The support structure 566 may be coupled to a distal end of a first tubing portion 568A. A proximal end of the first tubing portion 568A may be coupled to a compression fitting structure 570. The compression fitting structure 570 may be similar to the compression fitting structure 550 of FIG. 5C and the compression fitting structure 530 of FIG. 5B. The compression fitting structure 570 may couple an optical fiber tubing 572 and a second flexible tubing portion 568B together to permit an optical fiber pressure sensor to be deployed from the lumen 564 while also providing fluid into the eye 300. The proximal end of the second flexible tubing portion 568B includes a coupler 574 that may serve to connect the tubing portion 568B to a fluid source or to a console, such as the console 102, containing a fluid source. In some implementations, the coupler 574 may be a luer thread-style coupler.

Figure 6A:
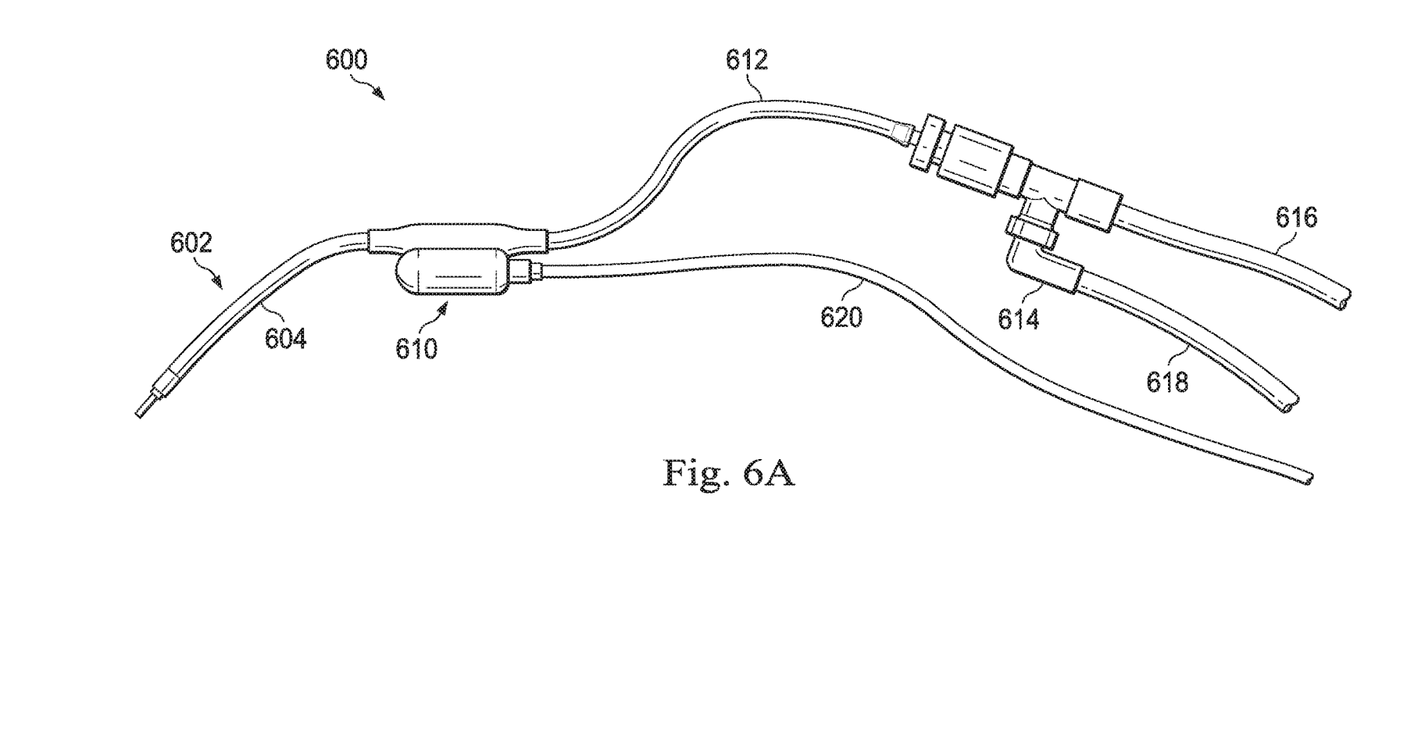
FIG. 6A is an illustration of an infusion line including a pressure sensing system.

FIG. 6A is an illustration of an exemplary infusion system 600 including a pressure sensing system 610. As shown in FIG. 6A, the exemplary infusion system 600 may include an infusion cannula 602 that may be similar in many respects to the infusion device 500 shown in FIG. 5A. The infusion cannula 602 is coupled by flexible tubing 604 to the pressure sensing system 610. The pressure sensing system 610 is shown in cross-section in FIG. 6B, and is coupled by a second flexible tubing 612 to an infusion valve 614. The infusion valve 614 may be an Auto-Infusion Valve developed by Alcon, Inc. of Fort Worth, Tex. The infusion valve 614 may be configured to couple to a liquid line 616 and a gas line 618 by a valve mechanism. The infusion valve 614 may controllably transition between the gas line 618 and the liquid line 616 to provide a gas infusion or a liquid infusion. For example, the surgeon may use the footpedal 114 of FIG. 1 to select between the gas line 618 and the liquid line 616 for infusion of gas or liquid into the eye 300. The pressure sensing system 610 may be coupled to an electrical line 620. The electrical line 620 may include power lines and/or signal lines that can be coupled to a pressure sensor contained within the pressure sensing system 610.

Figure 6B:
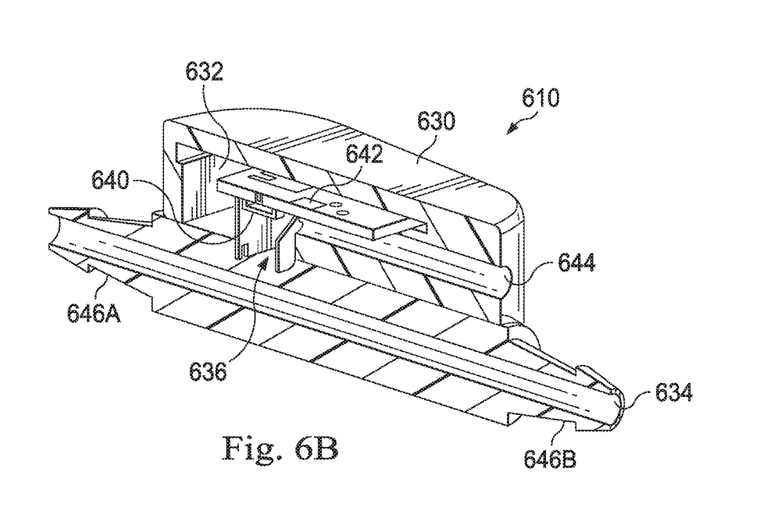
FIGS. 6B and 6C are illustrations of implementations of pressure sensing systems included in the infusion line of FIG. 6A.
Figure 6C:
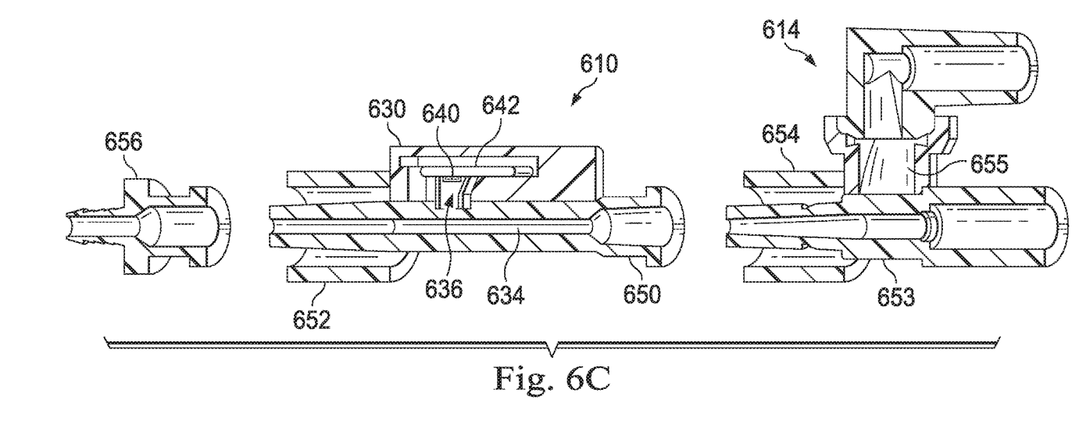

FIGS. 6B and 6C are illustrations of exemplary implementations of pressure sensing systems included in the exemplary infusion line of FIG. 6A. FIG. 6B shows the pressure sensing system 610 in cross-section. The pressure sensing system 610 includes a housing 630 having a chamber 632 and a flow channel 634 defined therein. A sensor exposure channel 636 couples to the flow channel 634 to expose the pressure sensor 640 to pressure within the flow channel 634. The pressure sensor 640 may be a MEMS pressure sensor disposed on sensor circuitry 642. Power lines and signal lines may be provided through the opening 644 in the sensor housing 630, like the electrical line 620 of FIG. 6A. The distal and proximal ends of the flow channel 634 may include an inlet connector 646A and an outlet connector 646B to permit the pressure sensing system 610 to be coupled to the flexible tubing 604 and the flexible tubing 612 of FIG. 6A.

FIG. 6C shows an additional implementation of the pressure sensing system 610. The implementation shown in FIG. 6C includes a proximal connector 650 and a distal connector 652 along the flow channel 634. The connectors 650 and 652 may permit the pressure sensing system 610 to be disposed close to the infusion valve 614, which is also shown in cross-section in FIG. 6C. The infusion valve 614 may include a valve body 653, having a valve mechanism 655, and a connector 654 that interfaces directly with the connector 650. The connector 652 may couple to a luer connector portion of a luer-to-barb type connector 656. The barb portion thereof may be coupled to flexible tubing, such as the flexible tubing 604 of FIG. 6A. Accordingly, implementations of the pressure sensing system 610 as shown in FIG. 6C may not include the second flexible tubing 612 of FIG. 6A.

Figure 7A:
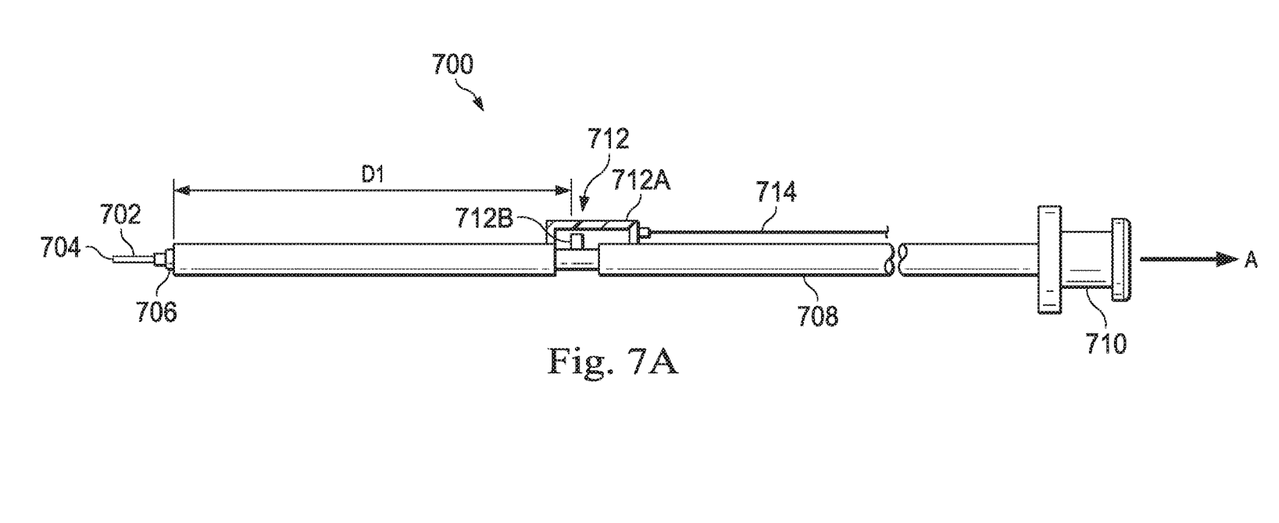
FIGS. 7A and 7B are illustrations of infusion lines including pressure sensing systems.
Figure 7B:
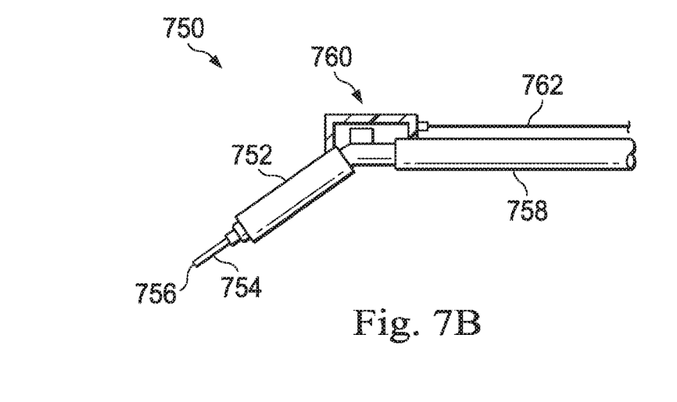

FIGS. 7A and 7B are illustrations of exemplary infusion lines including pressure sensing systems. FIG. 7A shows an exemplary infusion line 700. The infusion line 700 includes an elongate tubular member 702 having a lumen 704 formed therein. The elongate tubular member 702 is coupled to a support structure 706, which in turn is coupled to a distal end of flexible tubing 708. A proximal end of the flexible tubing 708 includes a connector 710, which may be used to couple the infusion line 700 to a console like the console 102 of surgical system 100, shown in FIGS. 1 and 2. Between the support structure 706 and the connector 710, a pressure sensor system 712 (shown in cross-section) may be affixed to the wall of the flexible tubing 708. The pressure sensor system 712 may include a housing 712A surrounding a sensor device 712B, such as a MEMS pressure sensor.

An opening in the wall of the flexible tubing 708 may expose the pressure sensor system 712 to a pressure within the lumen extending the length of the flexible tubing 708. The housing 712A may be affixed to an exterior surface of the flexible tubing 708, in some implementations. In other implementations, the housing 712A may be formed with a wall of the flexible tubing 708. As shown in FIG. 7A, the pressure sensor system 712 may be coupled to the console 102 by electrical lines 714. Some implementations of the exemplary infusion line 700 may include the electrical lines 714 being disposed outside of the flexible tubing 708. The electrical lines 714 may be secured to the flexible tubing 708 along at least some of the length thereof, in some implementations. In other implementations, the electrical lines 714 may be disposed within the wall of the flexible tubing 708. For example, the flexible tubing 708 may be formed by several layers of material deposited on top of each other, and the electrical line 714 may be disposed between two such layers. The pressure sensor system 712 may be offset from the support structure 706 by a distance D1. The distance D1 may range from about 2 inches to about 4 inches in some implementations. In other implementations, the pressure sensor system 712 may be positioned closer to or farther from the support structure 706.

FIG. 7B illustrates a portion of an infusion line 750. The infusion line 750 includes a rigid support structure 752 that is coupled to an elongate tubular member 754, having a lumen 756 extending therethrough. A proximal end of the rigid support structure 752 may be coupled to flexible tubing 758, which may have a connector, like the connector 710 of FIG. 7A or another suitable connector, at a proximal end thereof. The support structure 752 may be angled to facilitate placement near the eye 300. A pressure sensor system 760 (shown in cross-section) may be coupled to a central lumen of the support structure 752 by a channel through a wall of the support structure 752. Electrical lines 762 may couple the pressure sensor system 760 to transmit power to components of the pressure sensor system 760 and transmit measurement signals from the pressure sensor system 760.

In some implementations, the support structure 752 may have a straight configuration, without the bend or angle shown in FIG. 7B.

Figure 8A:
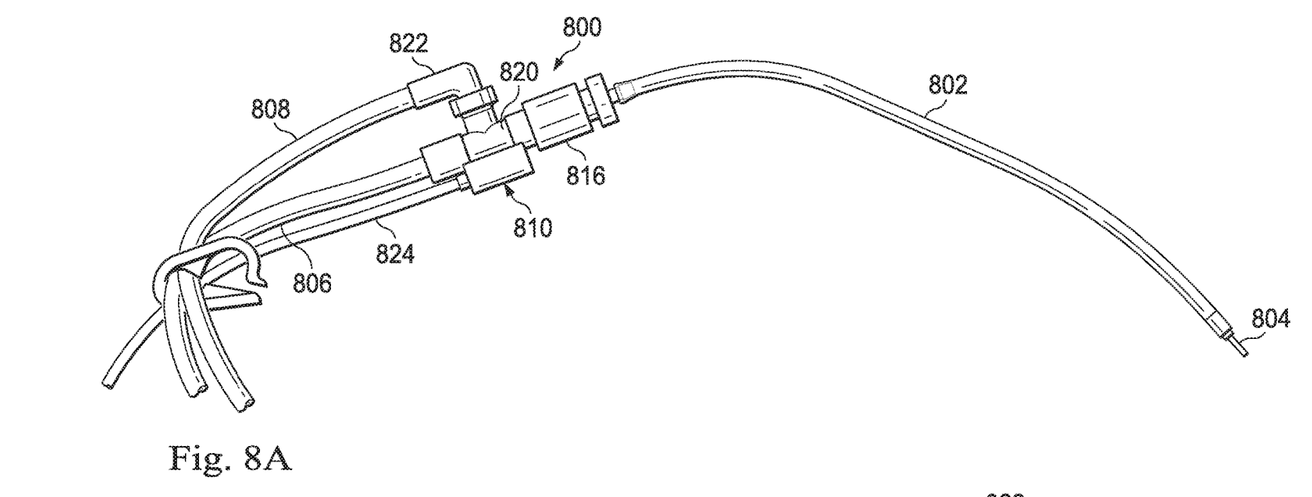
FIGS. 8A and 8B are illustrations of an infusion valve including a pressure sensing system.
Figure 8B:
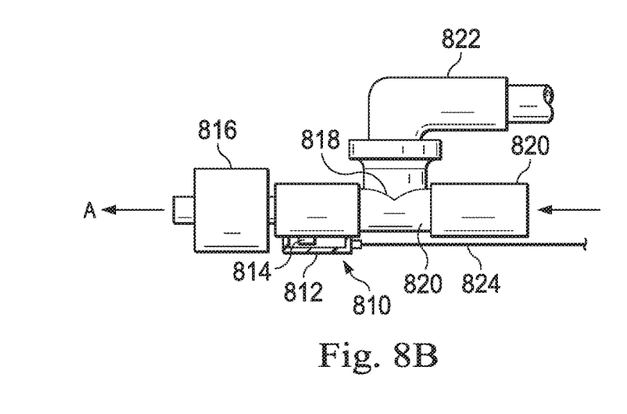

FIGS. 8A and 8B are illustrations of an exemplary infusion valve 800 including a pressure sensor system. The infusion valve 800 may permit a user to select between a gas source and a liquid source. A distal end of the infusion valve 800 may be coupled to flexible tubing 802, which connects to an infusion cannula 804 at a distal end thereof. The infusion valve 800 is further coupled to a liquid source by a liquid line 806 and a gas source by a gas line 808. The liquid source and the gas source may be included in the fluidics subsystem 120 shown in FIG. 2. The infusion valve 800 further includes a pressure sensor system 810.

The pressure sensor system 810 includes a sensor housing 812 that contains a pressure sensor 814. The sensor housing 812 may be formed integrally with the valve body, in some implementations. The pressure sensor 814 is in fluid communication with a channel extending through the valve 800. As illustrated, the pressure sensor 814, via the channel, is in communication with the lumen that extends through the valve 800 between a distal coupler 816 and a junction 818, where the liquid line portion 820 and the gas line portion 822 of the connect within the valve 800. Electrical lines 824 may connect to the pressure sensor 814 to a console, like the console 102. More specifically, the electrical lines 824 may connect the pressure sensor to the sensor subsystem 150, shown in FIG. 2. In this way, the valve 800 may provide pressure measurements indicative of a pressure within the valve 800. In some implementations, the valve 800 may be positioned less than 12 inches away from the infusion cannula 804 and the eye 300 of the patient. Accordingly, pressure measurements obtained when using the infusion valve 800 may be more accurate, in terms of absolute pressure measurements and transient pressure measurements, then estimates of pressure made within the console 102.

Figure 9:
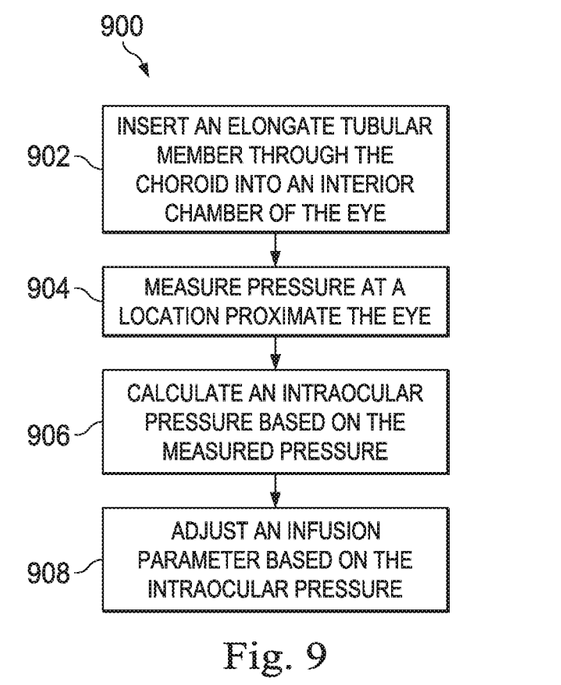
FIG. 9 is a flowchart of a method for measuring pressure inside an eye during an ophthalmic procedure.

FIG. 9 is a flowchart of an exemplary method for measuring pressure inside an eye during an ophthalmic procedure. Method 900 is illustrated in FIG. 9 as several enumerated operations or steps. Implementations of the method 900 may include additional operations, before, after, in between, or as sub-operations of the enumerated operations. Additionally, some implementations of the method 900 may omit one or more of the enumerated operations. At 902, an elongate tubular member may be introduced into the eye of a patient, as shown in FIG. 3. The elongate tubular member may be part of an ophthalmic device, like the devices 110 or 112 as shown, for example, in FIGS. 1, 3, 4B, 5A-D, 6A-C, 7A-B, and/or 8A-B. For example, the instrument may be or may include a drainage cannula, like the device 110 of, for example, FIGS. 1, 3, 5A-D, 6A-C, 7A-B, and/or 8A-B. As another example, the elongate tubular member may be part of an illumination probe like the device 112 shown, for example, in FIGS. 1, 3, and 4A-B. At least a portion of the elongate tubular member may be inserted through an entry cannula, like the entry cannulas shown in FIG. 3, or through an incision made through the sclera 304 as seen in FIG. 3. The distal region 206 of the instrument may be positioned proximate the retina 251.

At 904, a fluid pressure is measured at a location proximate the eye. For example, the device 110 or 112 may be used to measure pressure within an anterior chamber of the eye 300, as seen in FIG. 3. The pressure sensor may be part of a fiber-optic tip of an illumination probe or may be deployed through an infusion cannula, like the infusion devices 500, 520, 540, and 560 of FIGS. 5A-D. In other implementations, such as those shown, for example, in FIGS. 6A-C, 7A-B, and 8A-B, the pressure sensor may be deployed along a line extending between the console and a distal device tip. Accordingly, the pressure measurement may be obtained outside of the eye 300 but within about 12 inches from the eye 300, in some implementations. The pressure measurement may be obtained from within the infusion line, from within a pressure sensor housing disposed along portions of the infusion line, and/or within an infusion valve. By measuring the pressure either within the eye or a location less than 12 inches away from the eye, more accurate pressure measurements may be obtained. Because of their proximity to the eye 300, these pressure measurements may more accurately reflect the pressure within the eye 300 and may also more accurately and more quickly reflect pressure changes within the eye 300 or along the flexible tubing of an infusion device.

At 906, an intraocular pressure may be calculated based on the measured pressure. For example, the intraocular pressure may be calculated based on the measured pressure and an ambient pressure, such as atmospheric pressure. In some implementations, an estimate of the intraocular pressure may also be calculated based on flow rates into the eye and flow rates out of the eye. The measured intraocular pressure and the estimate of the intraocular pressure may be compared to check for discrepancies.

At 908, using an intraocular pressure calculated based on the measured pressure, a flow rate into or out of the eye 300 may be adjusted. In this way, the console 102 may operate to maintain a desired pressure within the eye 300 or maintain the pressure within the eye 300 in a desired pressure range. By maintaining the pressure at a desired level, the eye 300 may be prevented from collapsing and may also be prevented from exposure to high pressure levels which can cause permanent damage to the retina and other components of the eye, potentially leading to blindness.

The systems, devices, and methods described herein enable a user to obtain real measurements of pressure within the eye of a patient or measurements closer to the eye than conventional systems and devices currently allow. These systems, devices, and methods provide for more accurate pressure measurement which can improve efforts to maintain appropriate pressure levels within the eye during a procedure.

Persons of ordinary skill in the art will appreciate that the implementations encompassed by the present disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:
1. An ophthalmic device comprising:
an infusion cannula support structure having a proximal end coupled to a flexible tubing and a distal end coupled to a compression fitting structure;
an elongate tubular member extending from a distal end of the infusion cannula support structure, the elongate tubular member having a central lumen extending therethrough,
a pressure sensor disposed within the elongate tubular member such that when a distal end of the elongate tubular member is positioned within the eye, the pressure sensor is also positioned within the eye;

a first tubing coupled to the compression fitting structure, the first tubing having a lumen extending therethrough, the lumen of the first tubing fluidly coupled to and linearly arranged with the lumen of the elongate tubular member;

a second tubing coupled to the compression fitting structure, the second tubing having a lumen extending therethrough, the lumen of the second tubing disposed at a non-zero angle with respect to the lumen of the first tubing and the lumen of the elongate tubular member;

wherein the lumen of the first tubing, the lumen of the second tubing, and the lumen of the elongate tubular member are fluidly coupled to one another.

2. The ophthalmic device of claim 1, wherein the pressure sensor is moveable relative to the elongate tubular member to be extendable from the central lumen of the elongate tubular member and/or retractable into the central lumen.

3. The ophthalmic device of claim 2, wherein the pressure sensor is an optical fiber pressure sensor.

4. The device of claim 3 wherein the optical fiber pressure sensor is moveable within the lumen of the first tubing.

5. The ophthalmic device of claim 1, wherein the pressure sensor is affixed to a wall of the elongate tubular member.

6. The device of claim 1 wherein the lumen of the second tubing is configured to provide fluid to the eye or to aspirate fluid from the eye, and further wherein the irrigated or aspirated fluid passes through the lumen of the elongate tubular member.

7. An infusion and pressure sensing assembly comprising:
an infusion cannula comprising a first flexible tubing and a second flexible tubing;

a pressure sensor assembly comprising a housing, a flow channel extending through the housing, and a sensor exposure channel fluidly coupled to the flow channel;

a pressure sensor disposed within the housing and in fluid communication with the sensor exposure channel;

wherein a proximal end of the first flexible tubing is fluidly coupled to a first end of the flow channel and a distal end of the second flexible tubing is fluidly coupled to a second end of the flow channel.

8. The assembly of claim 7, wherein the sensor housing includes an inlet connector coupled to the second end of the flow channel and an outlet connector coupled to the first end of the flow channel.

9. The infusion line of claim 8, wherein the inlet connector and the outlet connector are luer connectors.

10. The infusion line of claim 7, further comprising at least one electrical line coupled through a wall of the sensor housing to the pressure sensor.

11. The assembly of claim 7 further comprising an infusion valve for liquid/gas exchange during an ophthalmic surgery, the infusion valve comprising:
a valve body;
a valve mechanism disposed within the valve body, wherein the valve mechanism is configured to facilitate transitions between gas infusion and liquid infusion;
a first inlet connector coupled to a gas source;
a second inlet connector coupled to a liquid source; and
an outlet connector for connection to an infusion line.

12. The assembly of claim 11 wherein the infusion valve is coupled to a second end of the second flexible tubing.

* * * * *